United States Patent [19]

Miguel-Colombel

[11] Patent Number: 5,750,120
[45] Date of Patent: May 12, 1998

[54] COSMETIC COMPOSITION IN THE FORM OF A SOLID DISPERSION COMPRISING A FATTY PHASE, A POLYHYDRIC ALCOHOL AND COLORLESS FILLERS

[75] Inventor: Dolores Miguel-Colombel, L'Hay-les-Roses, France

[73] Assignee: L'Oreal, Paris, France

[21] Appl. No.: 609,684

[22] Filed: Mar. 1, 1996

[30] Foreign Application Priority Data

Mar. 3, 1995 [FR] France .................. 95-02522

[51] Int. Cl.$^6$ .................. A61K 7/48; A61K 7/027
[52] U.S. Cl. .................. 224/401; 424/64; 424/69; 424/DIG. 5; 514/937
[58] Field of Search .................. 424/401, 64, 69, 424/DIG. 5; 514/937

[56] References Cited

U.S. PATENT DOCUMENTS 5,437,859  8/1995  Ser et al. .................. 424/59
5,580,546  12/1996  Ser et al. .................. 424/59

FOREIGN PATENT DOCUMENTS

| 524892 | 1/1993 | European Pat. Off. . |
| 609132 | 8/1994 | European Pat. Off. . |
| WO 94/06400 | 3/1994 | WIPO . |
| WO 94/06401 | 3/1994 | WIPO . |

*Primary Examiner*—Jyothsan Venkat
*Attorney, Agent, or Firm*—Finnegan, Henderson, Farabow, Garrett & Dunner, L.L.P.

[57] ABSTRACT

The present application relates to a cosmetic composition comprising a solid dispersion of at least one fatty phase and of at least one polyhydric alcohol, the composition being characterized in that it comprises colourless fillers and in that it contains no pigment.

15 Claims, No Drawings

COSMETIC COMPOSITION IN THE FORM OF A SOLID DISPERSION COMPRISING A FATTY PHASE, A POLYHYDRIC ALCOHOL AND COLORLESS FILLERS

The present invention relates to a cosmetic composition that may be applied to the skin, in particular to the lips, as a care and/or make-up product.

A cosmetic composition such as a lipstick, a blusher or a foundation, in the form of an anhydrous solid dispersion mainly comprising a polyhydric alcohol, at least one fatty constituent and usual inorganic and/or organic pigments, is known, for example from document FR 2,679,467, which corresponds to EP 0 524 892.

The term solid dispersion is understood to refer to a composition that is solid between 0°–50° C., which corresponds to the temperature range for storage and use of cosmetic products. These solid dispersions may be in the form of cast greasy products and, in particular, in the form of a stick, for lipstick in particular.

Now, it has been observed, quite surprisingly, that when one prepares a cosmetic composition similar to that described in this prior art, but free of pigment, that is to say of coloured filler usually employed as make-up colouring agent, the composition obtained no longer has the appropriate consistency; indeed, its consistency becomes very soft, to such a point that the composition, for example, one which is in the form of a stick of lipstick, may "crush" on the skin when it is applied. An excessive amount of product is thus placed on the lips in an uneven manner.

The aim of the present invention is to overcome this drawback and to propose a solid anhydrous dispersion that is free of pigments, while at the same time having an appropriate consistency that allows its application in the usual manner.

One subject of the present invention is an anhydrous cosmetic composition, free of pigments, comprising a solid dispersion of at least one fatty phase and of at least one polyhydric alcohol, characterized in that it comprises at least 5% by weight of colourless fillers.

The compositions according to the invention have good emollient properties when applied to the skin, as well as good staying power.

In the present specification, "pigment" means colored inorganic compounds used in cosmetics, especially in make-up products, for coloration purposes. For example, such pigments include iron oxide or chrome oxide.

Among the colourless fillers which may be incorporated into the composition according to the invention, mention may be made of inorganic fillers such as starch, optionally treated with octenylsuccinic anhydride, silica microspheres or silicone resin microbeads, and/or organic fillers such as nylon powder.

These fillers are present in a proportion of at least 5% by weight relative to the total weight of the composition, preferably in a proportion of 7–15%. They may, however, be present in considerable amounts, for example of the order of 28–30% by weight.

According to the invention, the fatty phase may comprise oils and/or waxes. The melting point of the fatty phase is preferably below 110° C. But some fatty phase components, such as waxes, could have a higher melting point.

It is preferable to use at least one wax with a melting point higher than 60° C. Among the oils that may be mentioned are:

mineral oils such as liquid paraffin or liquid petrolatum, animal oils such as perhydrosqualene or arara oil, plant oils such as sweet almond oil, calophyllum oil, palm oil, castor oil, avocado oil, jojoba oil, olive oil or cereal germ oils, silicone oils such as polydimethylsiloxane, esters of lanolic, oleic, lauric, stearic or myristic acid, for example, alcohols such as oleyl alcohol, linoleyl alcohol, linolenyl alcohol, isostearyl alcohol or octyldodecanol, alcohol or polyalcohol acetylglycerides, octanoates, decanoates or ricinoleates.

Among the waxes that may be mentioned are:

mineral waxes such as microcrystalline waxes, paraffin, petrolatum, vaseline, ozokerite and montan wax, animal waxes such as beeswax, and lanolin and its derivatives, plant waxes such as candelilla wax, carnauba wax, Japan wax and cocoa butter, hydrogenated oils, fatty esters and glycerides which are solid at 25° C., cetyl alcohol, stearyl alcohol and colophony and its derivatives.

The fatty phase may represent 20–94% by weight of the composition, preferably 40–85%.

According to the invention, the polyhydric alcohol may be a compound having 2–8 carbon atoms and 2–6 hydroxyl functions, such as ethylene glycol, glycerol, 1,2-propanediol, diglycerol, erythritol, arabitol, adonitol, sorbitol or dulcitol.

The polyhydric alcohol may also be a polyether alcohol with an average molecular weight of 150–600, such as polyethylene glycol 300 and polyglycerol 500.

The polyhydric alcohol may represent 0.5–50% by weight of the composition, preferably 5–30%.

Any additives usually used in the cosmetics industry may also be added, such as antioxidants, fragrances, preserving agents, cosmetic active agents, vitamins, essential fatty acids, sphingocerils, liposoluble sunscreens, surfactants, liposoluble polymers such as polyalkylenes, polyacrylates and silicone-containing polymers which are compatible with the fatty substances. These additives may be present in the composition in a proportion ranging from 0 to 10% by weight.

The composition according to the invention may be prepared in the usual manner according to the state of the art, by a person skilled in the art based on his general knowledge.

The composition according to the invention may be in the form of a care and/or make-up product, in particular in the form of a care base for the lips.

The invention will now be described in greater detail by means of the following examples, which are given solely by way of illustration and in no way limit the invention. The percentages are expressed as weight percentages.

EXAMPLE 1

A solid emulsion in the form of a lipstick having the following composition was prepared:

| | |
|---|---|
| • castor oil | 15% |
| • jojoba oil | 15% |
| • hydrogenated cocoa oil | 7.8% |
| • glyceryl tristearate | 3% |
| • isopropyl lanolate | 30% |
| • carnauba wax | 3% |

-continued

|                        |      |
|------------------------|------|
| • polyethylene wax     | 10%  |
| • glycerol             | 3%   |
| • silicone resin microbeads | 8%   |
| • antioxidant          | 0.2% |

The stick was prepared in the following manner: the fatty phase, on the one hand, and the polyhydric alcohol, on the other hand, were heated to a temperature of about 100° C., the filler was added and everything was then mixed together using a Moritz turbomixer at a speed of 3000 rev/min. The mixture was then poured into suitable moulds.

The composition obtained was anhydrous and colourless.

After 24 hours in an oven regulated to 34° C., the composition was still in the form of a stick of normal consistency and applied in the correct manner.

The treating base thus prepared is easy and pleasant to apply (soft and smooth).

EXAMPLE 2 (comparative example)

A solid emulsion in the form of a lipstick having the following composition was prepared:

|                          |      |
|--------------------------|------|
| • castor oil             | 17%  |
| • jojoba oil             | 17%  |
| • hydrogenated cocoa oil | 7.8% |
| • glyceryl tristearate   | 3%   |
| • isopropyl lanolate     | 34%  |
| • carnauba wax           | 3%   |
| • polyethylene wax       | 10%  |
| • glycerol               | 8%   |
| • antioxidant            | 0.2% |

The stick was prepared according to Example 1.

After 24 hours in an oven at 34° C., the composition crushed completely when applied to the lips, and it was found that half, if not all, of the stick was on the lips.

I claim:

1. An anhydrous cosmetic composition comprising a solid dispersion that comprises at least one fatty phase and at least one polyhydric alcohol, said composition further comprising at least 5% by weight of at least one colorless filler, and wherein said composition is free of pigment.

2. A composition according to claim 1, wherein said at least one colourless filler is starch, silica microspheres or silicone resin microbeads.

3. A composition according to claim 2, wherein the starch is treated with octenylsuccinic anhydride.

4. A composition according to claim 1, wherein said at least one colourless filler is nylon powder.

5. A composition according to claim 1, wherein said at least one colourless filler is present in a proportion of 5–30% by weight in the composition.

6. A composition according to claim 5, wherein said at least one colourless filler is present in a proportion of 7–15% by weight in the composition.

7. A composition according to claim 1, wherein the fatty phase is present in a proportion of 20–94% by weight in the composition.

8. A composition according to claim 7, wherein the fatty phase is present in a proportion of 40–85% by weight in the composition.

9. A composition according to claim 1, wherein said at least one fatty phase comprises at least one wax with a melting point above 60° C.

10. A composition according to claim 1, wherein said at least one polyhydric alcohol is a compound having 2–8 carbon atoms and 2–6 hydroxyl functions or a polyether alcohol having a weight average molecular weight of 150–600.

11. A composition according to claim 10, wherein said at least one polyhydric alcohol is ethylene glycol, glycerol, 1,2-propanediol, diglycerol, erythritol, arabitol, adonitol, sorbitol, dulcitol, polyethylene glycol 300, or polyglycerol 500.

12. A composition according to claim 1, wherein said at least one polyhydric alcohol is present in a proportion of 0.5–50% by weight in the composition.

13. A composition according to claim 12, wherein said at least one polyhydric alcohol is present in a proportion of 5–30% by weight in the composition.

14. A care and/or make-up product for the skin comprising an anhydrous cosmetic composition according to claim 1.

15. A care base for the lips comprising an anhydrous cosmetic composition according to claim 1.

* * * * *